(12) United States Patent
Liu et al.

(10) Patent No.: US 8,404,192 B2
(45) Date of Patent: Mar. 26, 2013

(54) BIOCHIPS AND RELATED AUTOMATED ANALYZERS AND METHODS

(75) Inventors: Ben H. Liu, Raleigh, NC (US); Meghan E. Vidt, Winston-Salem, NC (US); Jeffrey R. Soohoo, Raleigh, NC (US)

(73) Assignee: Ben H. Liu, Raleigh, NC (US)

( * ) Notice: Subject to any disclaimer, the term of this patent is extended or adjusted under 35 U.S.C. 154(b) by 797 days.

(21) Appl. No.: 12/428,718

(22) Filed: Apr. 23, 2009

(65) Prior Publication Data
US 2009/0270274 A1 Oct. 29, 2009

Related U.S. Application Data

(60) Provisional application No. 61/047,788, filed on Apr. 25, 2008.

(51) Int. Cl.
*G01N 33/00* (2006.01)

(52) U.S. Cl. ......... 422/502; 422/503; 422/551; 422/552

(58) Field of Classification Search .................. 422/502, 422/503, 551, 552
See application file for complete search history.

(56) References Cited

U.S. PATENT DOCUMENTS

| | | | |
|---|---|---|---|
| 6,924,107 B2 | 8/2005 | Liu | |
| 7,112,433 B2 | 9/2006 | Tyvoll et al. | |
| 7,235,389 B2 | 6/2007 | Lim et al. | |
| 7,300,755 B1 | 11/2007 | Petersdorf et al. | |
| 7,740,806 B2 * | 6/2010 | Natarajan | 422/404 |
| 2006/0105449 A1 | 5/2006 | Larmer et al. | |
| 2007/0092975 A1 | 4/2007 | Potyrailo et al. | |

OTHER PUBLICATIONS

International Search Report and Written Opinion for corresponding PCT Application No. PCT/US2009/002510, date of mailing Dec. 18, 2009.

* cited by examiner

*Primary Examiner* — Sam P Siefke
(74) *Attorney, Agent, or Firm* — Myers Bigel Sibley & Sajovec, P.A.

(57) ABSTRACT

The present invention provides biochips that include: (a) a plurality of cards, each card having a plurality of card apertures extending therethrough, each respective card aperture having one or more cross sectional areas; and (b) a plurality of gaskets, at least one gasket residing intermediate two neighboring cards, each gasket having a plurality of gasket apertures extending therethrough. At least some of the gasket apertures have an area that is greater than that of at least one adjacent card aperture. Different sets of the gasket apertures and card apertures define a plurality of fluidic flow channels. Also provided herein are methods of making and using biochips.

19 Claims, 12 Drawing Sheets

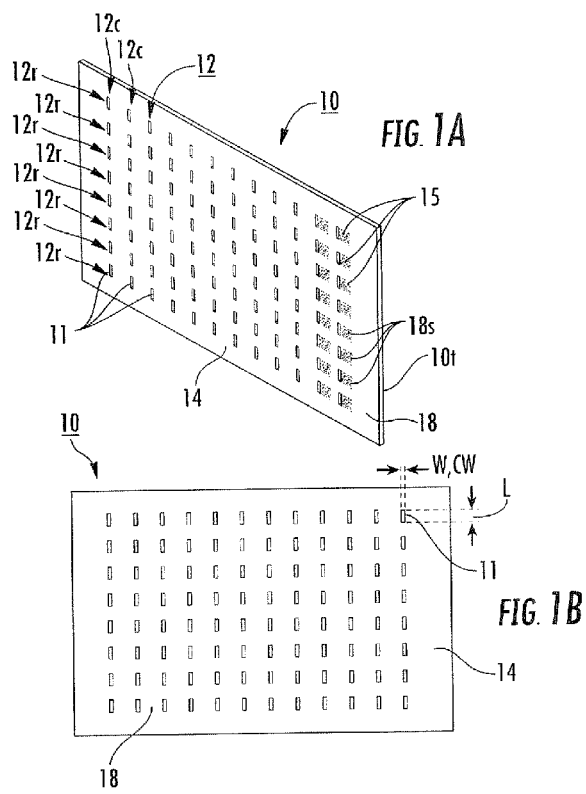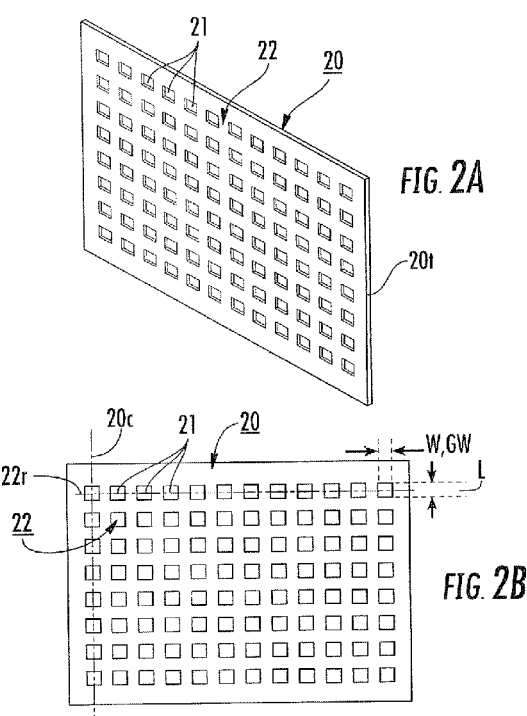

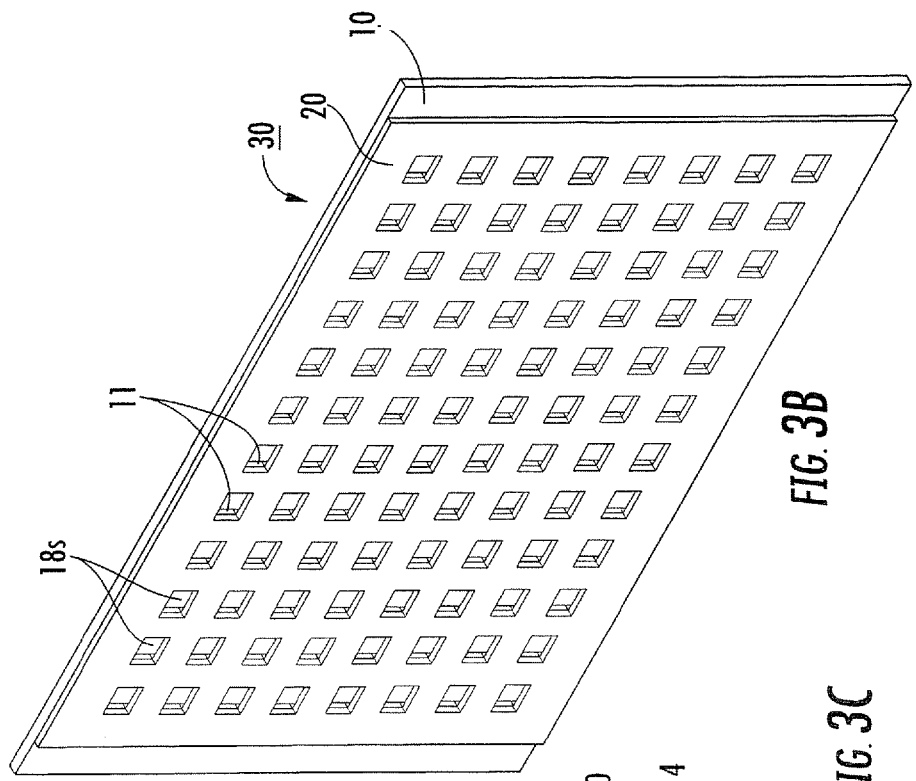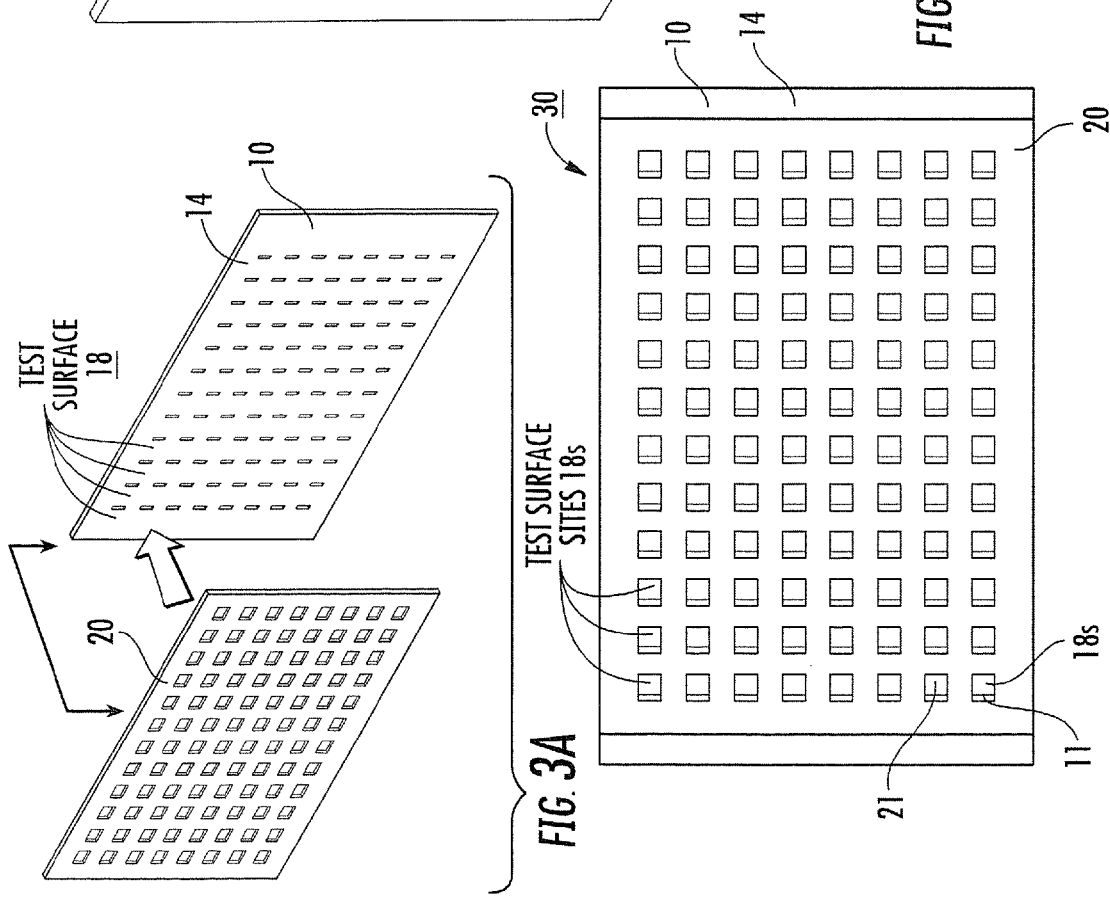

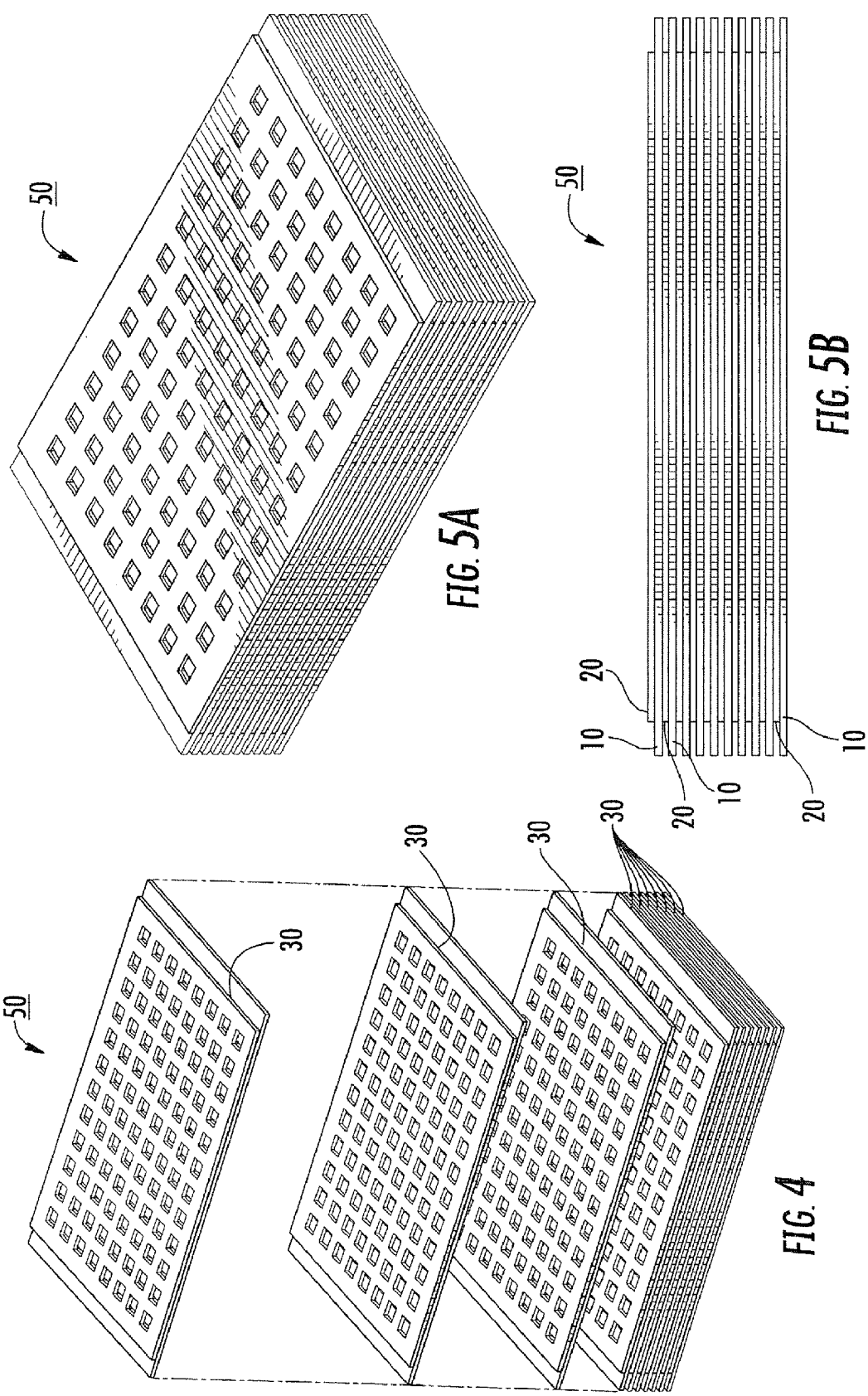

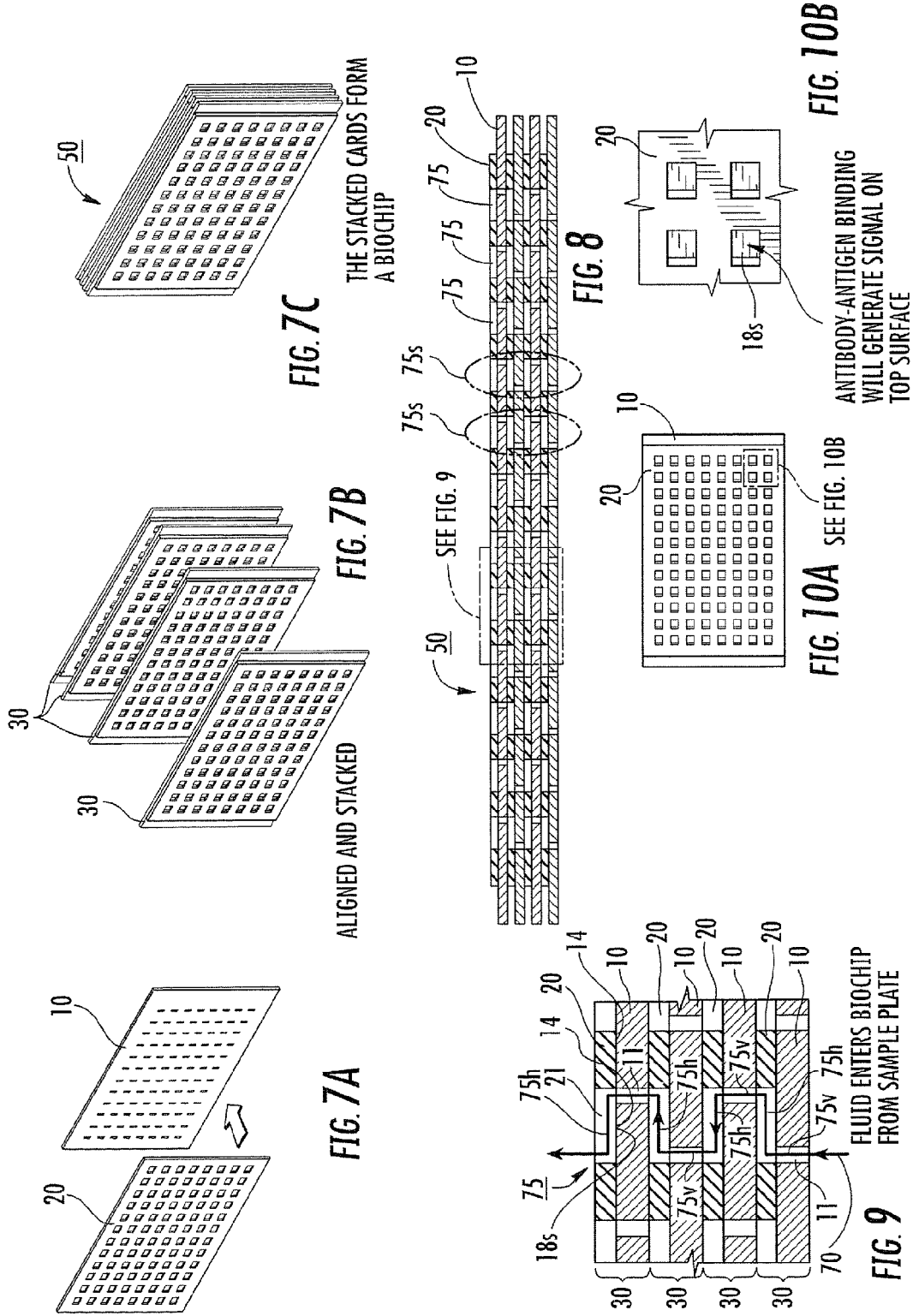

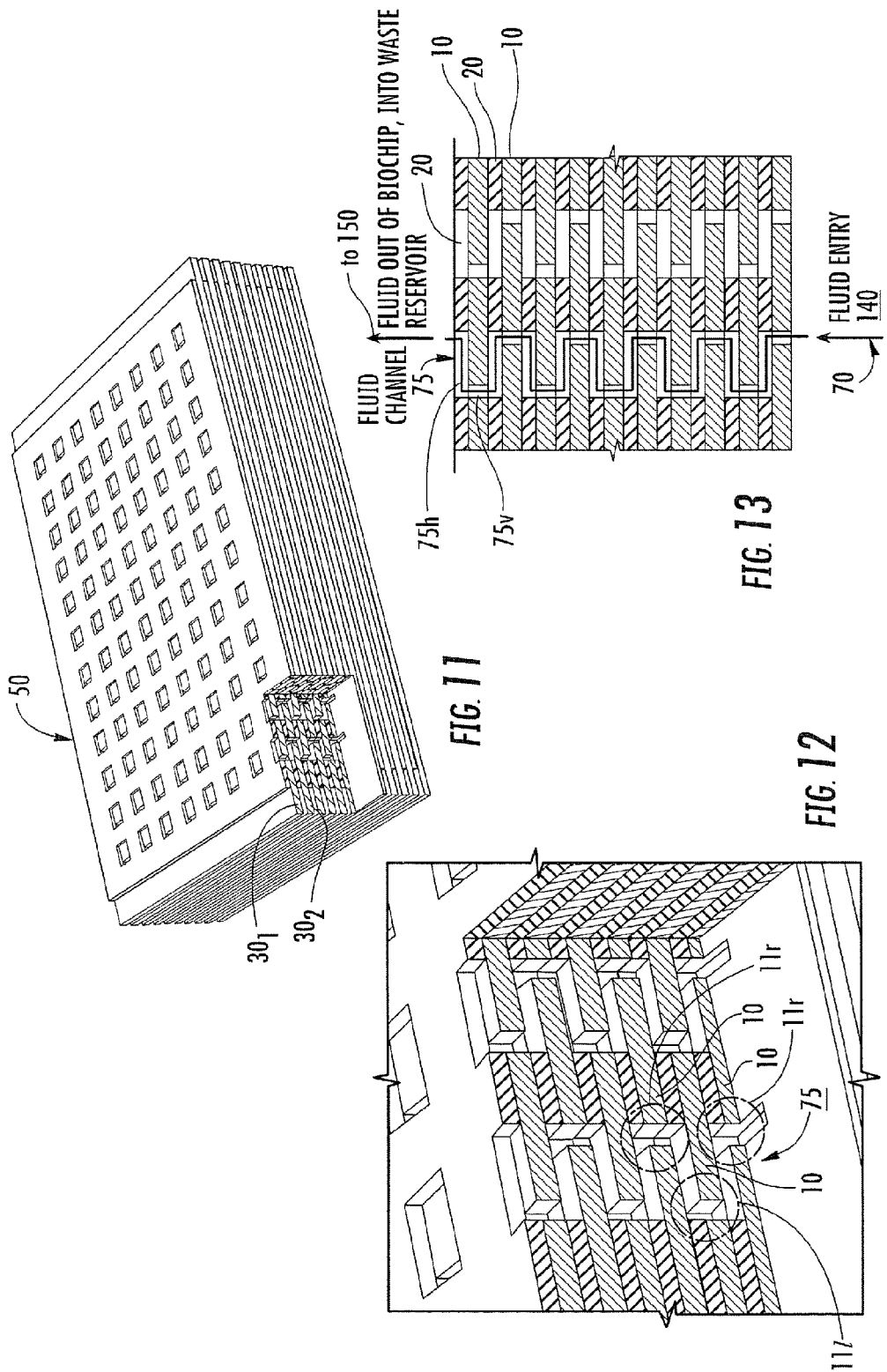

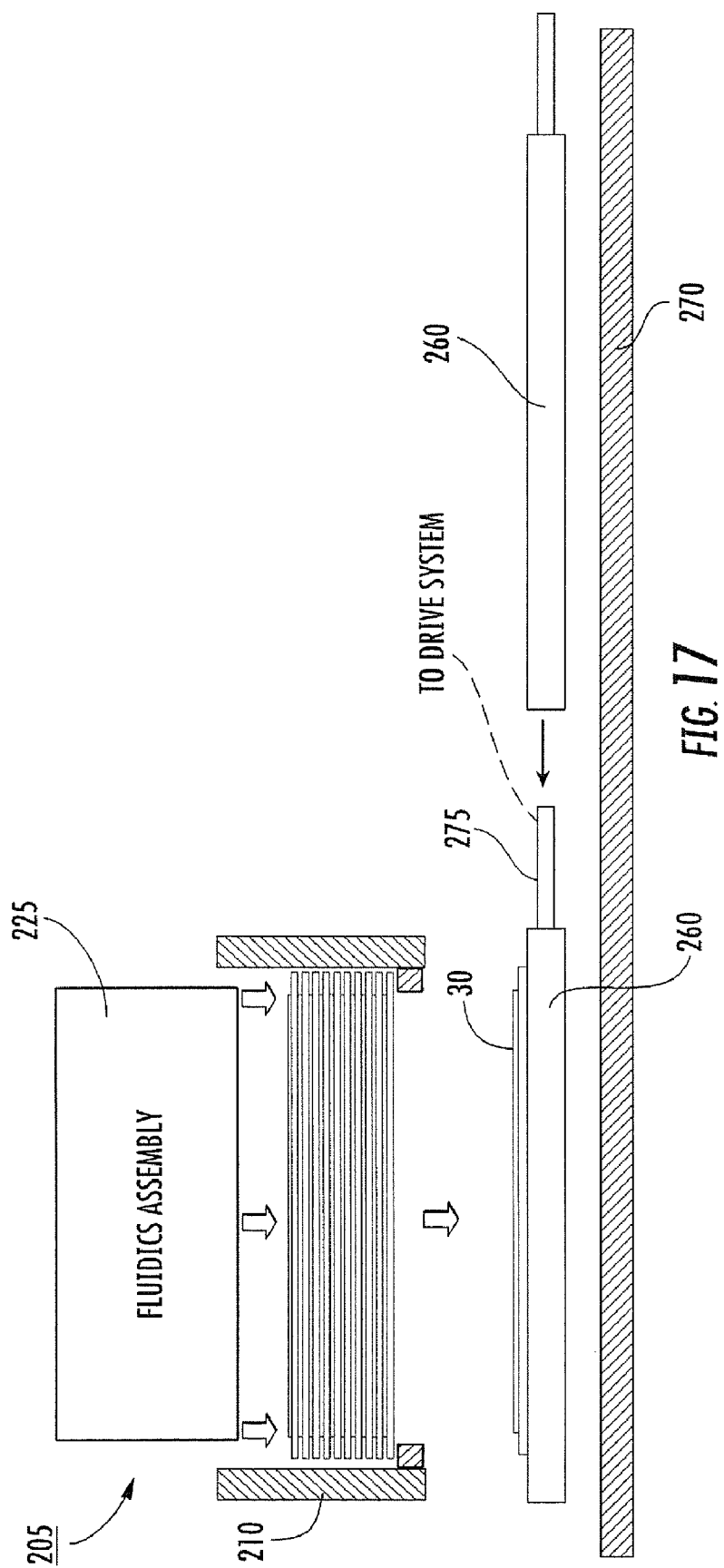

BIOCHIPS AND RELATED AUTOMATED ANALYZERS AND METHODS

RELATED APPLICATION

This application claims the benefit or priority of U.S. Provisional Application Ser. No. 61/047,788, filed Apr. 25, 2008, the contents of which are hereby incorporated by reference as if recited in full herein.

FIELD OF THE INVENTION

The present invention relates to biochips and automated analyzers thereof.

BACKGROUND

Large scale, multiple sample, parallel biochemistry assays, automated instruments and system integration using bioinformatics technologies are key factors for advancing the fields of low and high throughput analysis and diagnosis. Biochip technology has become increasingly more popular, with one major goal being efficient and economical measurement of multiple samples for biological parameters, in the research environment, as well as in clinical diagnostics.

SUMMARY OF EMBODIMENTS OF THE INVENTION

Embodiments of the present invention are directed to biochips, biochip analyzers and methods of making and analyzing biochips.

In some embodiments, the biochip includes a plurality of cards, each card having a plurality of card apertures extending therethrough and each respective card aperture having one or more cross sectional areas, and a plurality of gaskets, at least one gasket residing intermediate two neighboring cards. The cards and gaskets have a plurality of apertures extending therethrough. At least some of the gasket apertures can have a cross-sectional area that is greater than that of at least one adjacent card aperture. Sets of the gasket apertures and card apertures define a plurality of fluidic flow channels.

In some embodiments of the biochip, the gaskets can be flexible and the cards can be rigid. The cards and gasket members can be releasably attached and held together in a stack to define microfluidic flow channels. At least some of the flow channels can have a repeating pattern of alternating substantially horizontal and substantially vertical segments along substantially an entire length thereof, with at least one of the horizontal segments associated with an upper or lower surface of a respective card defining a horizontal test surface that contacts a flowing test sample at each layer of the stacked biochip.

In further embodiments, one gasket can be affixed to one card to define an integral gasket/card pair, with one gasket aperture aligned with a corresponding card aperture. A plurality of the gasket/card pairs can be releasably engaged and held together during use to define the plurality of fluidic flow channels.

A biochip according to embodiments of this invention can also comprise gaskets that are configured with an array of gasket apertures with substantially all or all of the gasket apertures having the same shape and size, and the cards can be configured with an array of card apertures with substantially all or all of the card apertures having the same shape and size. The gasket apertures can have a box shape, and the card apertures can be substantially rectangular with a length dimension thereof being greater than a width dimension thereof.

In further embodiments, a biochip with multiple cards is configured so that at least some of the cards include at least one bioactive material and/or coating on at least one of an upper and lower surface that contacts a sample flowing thereover and different cards can have different bioactive coatings and/or materials to conduct multiple analyses.

In some embodiments, biochips can have a plurality of different analytical sites, with at least one on each card and the plurality of fluidic flow channels can be in fluid isolation and configured to analyze a plurality of different samples.

In particular embodiments, a biochip is provided, with a plurality of discrete microfluidic flow channels that can be configured to concurrently flowably receive a plurality of different samples, one through each microfluidic flow channel, whereby the respective samples are contacted with a plurality of different analytical sites, with at least one analytical site on each card in an area of the card on an upper or lower surface exposed by an aligned gasket aperture.

Additional embodiments of the invention include biochips that include a plurality of releasably engageable stacked cards with at least one gasket between neighboring cards and the layers of gasket and cards defining microfluidic flow channels. The channels can extend upward or downward for a first distance corresponding to a thickness of a first card, laterally for a second distance along a substantially horizontal surface of the first card, the second distance corresponding to a width of a first gasket aperture, then extend upward or downward for a third distance corresponding to a thickness of a second card, then laterally for a fourth distance along a substantially horizontal surface of the second card, the fourth distance corresponding to a width of a second gasket aperture.

The gasket apertures of the biochip can have a box shape and the card apertures can have a box shape. In some embodiments, the card apertures can have a rectangular shape, with a width dimension of the card apertures being a minor portion of a width dimension of the gasket apertures, and with a length dimension of the card apertures being substantially the same as a length dimension of the gasket apertures. The stacked cards and gaskets can define closely spaced microfluidic flow channels, wherein each channel is configured so that a fluid can travel through the channel substantially vertically for the first distance, substantially horizontally for the second distance, substantially vertically for the third distance, and substantially horizontally for the fourth distance. In such embodiments, one or more of the cards can comprise one or more bioactive coatings and/or materials.

Yet other embodiments of the invention are directed to biochip subassemblies. The subassemblies include a flexible gasket having an array of substantially box shaped apertures and a substantially rigid card affixed to the flexible gasket. The card can have a bioactive material and/or coating thereon and an array of substantially rectangular shaped card apertures with a width dimension being less than a width dimension of the gasket apertures. The gasket resides over the card such that a respective gasket aperture resides over a corresponding card aperture with the card aperture residing proximate a side edge of the gasket aperture. A surface of the card under the gasket aperture is exposed through the gasket aperture and is accessible for contact with a fluid sample.

Also provided in embodiments of this invention are biochips with a plurality of the biochip subassemblies described herein, in a stacked relationship and arranged so that adjacent first and second biochip subassemblies are configured with the first biochip subassembly having first card apertures positioned proximate a left side of first gasket apertures and the second biochip subassembly having second card apertures positioned proximate a right side of second gasket apertures. The biochips can also be configured with a surface of the card having predetermined optically and/or electronically readable indicia.

Yet other embodiments of the present invention include biochips with a plurality of stackable card/gasket members, each card/gasket member having an opposing upper and lower surface and a plurality of apertures extending therethrough, the stackable members being aligned so that the apertures define microfluidic flow channels. At least some of the channels have alternating substantially horizontal and substantially vertical surfaces, with at least some of the horizontal surfaces defining one or more analytical sites.

Yet other embodiments of the present invention are directed to automated or semi-automated analyzers. The analyzers include: (a) a biochip having a plurality of microfluidic flow channels extending through a plurality of releasably attached cards, with at least some of the cards having a bioactive agent and/or material; (b) a card separation and holding member configured to obtain one card from the releasably attached cards of the biochip and move the obtained card to a reading station; (c) a reader at the reading station configured to communicate with the obtained card in the reading station and obtain a signal of at least one analytical site of the card; and (d) a control circuit configured to direct automated operation of the separation member and reader.

The system can also include an analyzer in communication with the reader that programmatically analyzes the obtained signal of the at least one analytical site.

The system may also include a fluid delivery system in communication with an upper or lower portion of the biochip for flowing fluid samples and/or solutions through the biochip.

The bioanalyzer can also include a control circuit comprising a controller that is configured to direct the signal reader to obtain signal from a region of each card that comprises predetermined readable indicia, which can be used to verify the identity and/or authenticity of the card and optionally block operation if the card is not verified to thereby inhibit the use of unauthorized biochips.

Further embodiments of this invention include a method of fabricating a biochip, comprising: (a) providing a first rigid card having an array of card apertures extending therethrough, the first card having at least one bioactive material and/or coating; and (b) attaching a first gasket to the first card to form a first card/gasket pair, (for example, by co-molding, adhesive attachment, frictional engagement, clamping, etc.,) the first gasket having an array of gasket apertures extending therethrough, and the gasket apertures having a larger cross-sectional area than the card apertures, so that the gasket apertures overlay the card apertures with the card apertures residing proximate one side edge of the gasket apertures with a surface of the first card exposed under the gasket apertures and defining a horizontal surface of a microfluidic flow channel. The methods of fabricating a biochip of this invention can further comprise repeating steps (a) and (b) a plurality of times to produce a plurality of card/gasket pairs and assembling the pairs to produce a multi-layered releasably attached stacked biochip with microfluidic flow channels with alternating substantially horizontal and substantially vertical surfaces.

In some embodiments of fabricating methods of this invention, a first card/gasket pair can be configured with a first card aperture located proximate the left side of a first gasket aperture and a second adjacent card/gasket pair can be configured with a second card aperture located proximate the right side of a second gasket aperture to define a microfluidic flow channel with alternating substantially horizontal and substantially vertical surfaces.

Further embodiments of this invention include an automated method of analyzing multiple samples in a single biochip, comprising: a) introducing a multiplicity of fluid samples into a fluid delivery system of an automated bioanalyzer; b) flowing the multiplicity of fluid samples through a biochip having a plurality of releasably attached card/gasket pairs, each of the card/gasket pairs having an aligned array of apertures extending therethrough, wherein sets of the apertures define microfluidic flow channels, with each card comprising at least one analytical site in the channels proximate the card apertures; c) serially obtaining and presenting a card of the biochip to a signal reader configured to selectively engage at least one analytical site of the card and obtain a signal from the analytical site; d) selectively engaging the at least one analytical site of the respective cards and obtaining a signal from the analytical site; and e) analyzing the obtained signal(s).

At least one card of the biochip can comprise at least one bioactive material and/or coating on at least one of an upper and lower surface that contacts a fluid sample flowing thereover. Such bioactive material and/or coating can be, but is not limited to, an antibody, an antigen, a nucleic acid, a peptide nucleic acid, a ligand, a receptor, avidin, biotin, Protein A, Protein G, Protein L, a substrate for an enzyme and any combination thereof.

In some embodiments the bioreactive material can be an antigen and a signal is detected if an antigen/antibody complex is formed. In other embodiments, the bioreactive material can be an antibody and a signal is detected if an antigen/antibody complex is formed. In further embodiments, the bioreactive material can be a nucleic acid or peptide nucleic acid and a signal is detected if a hybridization complex is formed.

Embodiments of this invention are directed to biochips that can be assembled in a scalable configuration to include a selectable plurality of cards and gaskets (e.g., as card/gasket pairs), x, wherein x is an integer from one to 100,000. The selection can be by end user or OEM based on the tests desired or applications. The biochips can be provided as kits, with cards, gaskets or card/gasket pairs that can be assembled by the purchaser or end user. The biochips may also comprise a plurality of card apertures, y, wherein y is an integer from one to 100,000, typically between about one and about 1536, depending on card size. In addition, the biochips may also comprise a plurality of gasket apertures, z, wherein z is an integer from one to 100,000, again, typically between about one and about 1536, depending on gasket size.

In further embodiments of the biochips, each card of the plurality of cards can have the same number of card apertures and in some embodiments, each gasket of the plurality of gaskets can have the same number of gasket apertures. In particular embodiments, the number of card apertures of each card can be equal to the number of gasket apertures of each gasket.

It is noted that features of embodiments of the invention as described herein may be methods, systems, computer programs or a combination of same although not specifically stated as such. The above and other embodiments will be described further below.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 1A is an isometric view of a card of a biochip according to embodiments of the present invention.

FIG. 1B is a top view of the card shown in FIG. 1A.

FIG. 2A is an isometric view of a gasket of a biochip according to embodiments of the present invention.

FIG. 2B is a top view of the gasket shown in FIG. 2A.

FIG. 3A is an isometric exploded view of a gasket and a card pair according to embodiments of the present invention.

FIG. 3B is an isometric view of a biochip subassembly comprising the gasket and card pair shown in FIG. 3A according to embodiments of the present invention.

FIG. 3C is a top view of a biochip subassembly shown in FIG. 3B.

FIG. 4 is a partially exploded perspective view of a plurality of biochip subassemblies of FIG. 3B shown in a stackable relationship according to embodiments of the present invention.

FIG. 5A is a perspective view of a biochip made up of stacked biochip assemblies according to embodiments of the present invention.

FIG. 5B is a front view of the biochip shown in FIG. 5A.

FIGS. 7A-7C are isometric views of operations that can be used to form a biochip. FIG. 7A illustrates forming a gasket and a card biochip subassembly according to embodiments of the invention. FIG. 7B illustrates aligning and stacking gasket and card pairs according to embodiments of the present invention. FIG. 7C illustrates the aligned cards of FIG. 7B stacked together.

FIG. 8 is an enlarged section view of a biochip illustrating fluid channels according to embodiments of the present invention.

FIG. 9 is a greatly enlarged partial side view of the biochip shown in FIG. 8 illustrating an exemplary direction of flow of a fluid sample through a flow channel according to embodiments of the present invention.

FIG. 10A is a top view of one of the biochip subassemblies shown in FIG. 6 illustrating a post-exposure condition of the analytical sites of the card according to embodiments of the present invention.

FIG. 10B is an enlarged partial top view of the biochip subassembly of FIG. 10A, showing one of the analytical sites with an exemplary reaction to the fluid sample according to embodiments of the present invention.

FIG. 11 is a perspective partial cutaway view of a biochip showing two adjacent fluidic flow channels within the biochip according to embodiments of the present invention.

FIG. 12 is a greatly enlarged perspective view of the cut away section of the embodiment shown in FIG. 11 illustrating aligned gasket apertures and card apertures defining alternate sides of a flow channel of a biochip according to embodiments of the present invention.

FIG. 13 is a schematic of a portion of a biochip illustrating one flow channel according to embodiments of the present invention.

FIG. 17 is a schematic illustration of an automated or semi-automated biochip analyzer system illustrating the holding member shown in FIGS. 15A and 15B in communication with the holder shown in FIG. 14 according to embodiments of the present invention.

DETAILED DESCRIPTION OF EMBODIMENTS OF THE INVENTION

Figure 6:
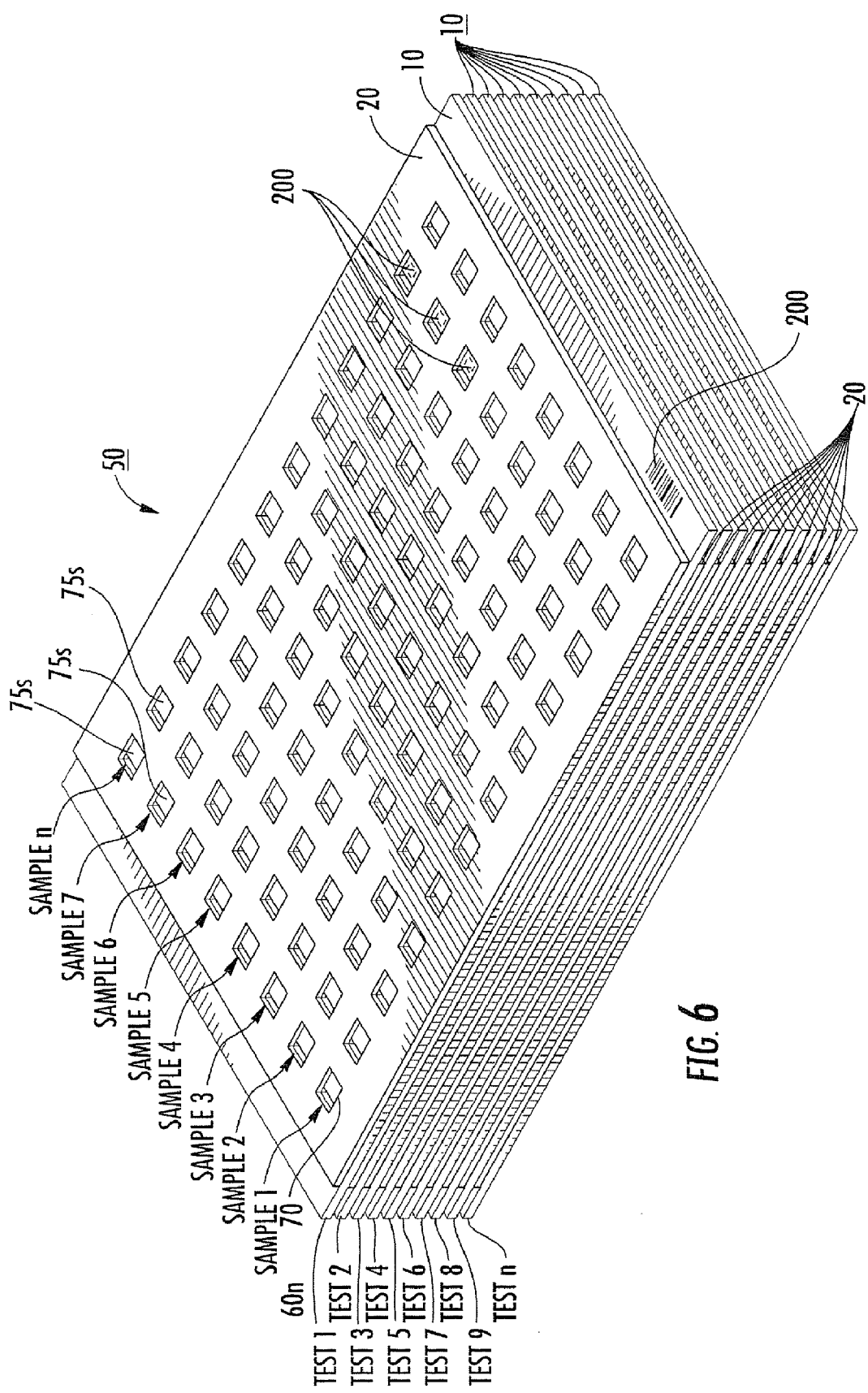
FIG. 6 is an enlarged perspective view of the biochip shown in FIG. 5B made showing different samples can flow through different flow channels according to embodiments of the present invention.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Also as used herein, phrases such as "between X and Y" and "between about X and Y" should be interpreted to include X and Y. Furthermore, phrases such as "between about X and Y can mean "between about X and about Y" Also, phrases such as "from about X to Y" mean "from about X to about Y."

Further, the term "about" as used herein when referring to a measurable value such as an amount or numerical value describing any sample, flow rate, composition or agent of this invention, as well as any dose, time, temperature, and the like, is meant to encompass variations of ±20% or lower, such as, for example, ±10%, ±5%, ±1%, ±0.5%, or even ±0.1% of the specified amount.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

The term "biochip" refers to a device having one or more analytical sites arranged on and/or in one or more substrates that permits one or more analyses to be performed on one or more fluid samples (e.g., microsamples) at the same time and/or at different times, typically via flowable throughput through fluidic channels in the device. The fluid test sample can be in substantially gas or liquid form, but is typically liquid. The test sample may include solid or particulate matter in the fluid. The flowable throughput may, in some embodiments, be high throughput conditions at a rapid flow rate(s). Flow speed can ranges from about 1 µl per minute for a simple flow through assay (e.g., sample passes through the channel slowly and no incubation is needed) to about 10 ml per minute (or more) for some assays. The biochip is typically configured to concurrently accept and test multiple different samples and perform multiple different analyses on those samples.

A "fluidic flow channel" refers to a continuous or uninterrupted fluid pathway or channel through the biochip with an opening at either end or top or bottom of the biochip (i.e., an inlet and an outlet) to allow the passage of fluid therethrough from a sample entry location to a sample discharge location. A "microfluidic" flow channel is a miniaturized fluidic flow channel that accommodates a small fluid volume, typically between microliters and nanoliters of fluid. The microfluidic flow channel typically can hold or accommodate microscale amounts (e.g., microliters or less, such as, for example, in nanoliters to microliters) of fluid, which can be in the form or a gas or liquid as noted above. In some embodiments, each channel can, for example, hold from a sub-microlitre (e.g., about 0.1 µl) to about 100 µl volume. In some embodiments, for example, a channel can hold between about a 1 µl to about a 10 µl volume. For example, if one channel holds about 2 µl of liquid, it can process about 40 µl of sample to test 20 analytes.

The term "card" refers to a substrate of the biochip that typically provides an analytical site or sites. The card can comprise a rigid material or a substantially rigid material that resists flexure when unassembled (e.g., has sufficient rigidity to maintain its shape in free space). The card can be in any suitable geometric configuration or shape and have any suitable thickness or thicknesses. The card can comprise any suitable material such as, for example, a metal, a glass, a ceramic, a polymer or combinations thereof and may be opaque, translucent or transparent. The card can be formed of a single layer substrate of a single material or a laminated or multi-layer configuration of the same or different material substrates. The polymer may be a thermoplastic polymer such as, for example, polystyrene. The card is typically a single layer monolithic substrate having a thickness that is between about 0.2 mm to about 15 mm, and is more typically between about 1 mm to about 12 mm. The card can comprise a bioactive agent that is formed in a matrix of the substrate and/or applied or coated on a primary surface thereof to define one or more analytical sites on the card for analysis of one or multiple different samples.

The term "bioactive" includes the term "bioreactive" and means an agent or material or composition that alone or when combined with another agent and exposed to a test sample will form a chemical reaction and/or be altered in appearance or in another optical or electronically readable or detectable manner when a target analyte, e.g., constituent, antigen, antibody, bacterium, virus, ligand, protein contaminant, toxin and/or other material is present in the test sample. See, e.g., U.S. Pat. No. 6,924,107, the contents of which are hereby incorporated by reference as if recited in full herein.

The term "gasket" refers to a member of a biochip that cooperates with one or more cards to define a substantially fluid tight seal between adjacent cards. The gasket can be any suitable material, such as, for example, a polymer, rubber, and metal. The gasket may have a thickness that is substantially the same, more or less than a neighboring card. In some embodiments, the gasket is formed of an elastically compressible material. In some embodiments, thermoplastic elastomers (including but not limited to Viton®, Buna-N®, EPDM®, and Versaflex®) and/or silicone rubbers can be used for fabricating the gasket.

Turning now to the figures, FIGS. 1A and 1B illustrate an exemplary card 10 with card apertures 11. The card apertures 11 can be arranged in any manner. As shown, the apertures 11 are configured in an array 12 of aligned columns 12c and rows 12r. In position (when assembled as will be discussed further below), the apertures 11 can define portions of different and discrete flow channels or may cooperate to form a single or multiple flow channels. As shown, the card 10 can have a substantially rectangular shape, but other shapes may be used as well.

FIG. 1A illustrates that at least one primary surface 14 of the card 10 can include at least one bioactive material 15 forming the test surface 18 with analytical test sites 18s. The material 15 can be applied or integrated in any suitable manner. For example, the material 15 can be formed into or on the substrate of the card or as a coating thereon. Thus, the card 10 or portions thereof can be coated, covered, impregnated, vapor deposited, permeated, plated, soaked and/or embedded with a bioactive agent or material 15. The material 15 can also be applied by a shrink-wrap or adhesively attachable strip or patch.

The material 15 can reside on or over substantially all or all of one or both primary surfaces or applied selectively adjacent one or more of the apertures 11. It is to be understood that the one or more than one analytical site 18s can be located on either surface (e.g., top, bottom) or both the top and bottom primary surface of the card. In some embodiments, a first bioactive agent or material can be present on a first surface of the card and a second bioactive agent or material can be present on a second surface of the same card. In certain embodiments, the card is immersed or soaked in a solution comprising the bioactive agent or material, resulting in the presence of the bioactive agent or material on both upper and lower (top and bottom) surfaces of the card, as well as on the surfaces lining the apertures.

The same material 15 can be applied to the entire primary surface 15 or proximate each aperture 11 on a respective card or different materials 15 or combinations of materials can be applied to different aperture locations on a respective primary card surface 14 in any combination. The material 15 can be integrated with or applied to both the opposing primary surfaces (not shown). Each card 10 in a biochip 50 (FIGS. 4, 5A, 5B) can have the same or a different material 15.

FIG. 1B illustrates that each aperture 11 can have substantially the same width "W" and length "L" and that each aperture 11 can have the same geometric shape, e.g., a box-like shape, typically a rectangular shape with a length dimension being greater than a width dimension, although the reverse configuration or different shapes and dimensions may also be used. The width of the card aperture(s) 11 can also be called "CW." In particular embodiments, the card 10 can have a thickness 10t (FIG. 1A) that is between about 0.2 mm to about 12 mm.

FIGS. 2A and 2B illustrate a gasket 20 with apertures 21. The gasket apertures 21 can be arranged in any manner. As shown, the apertures 21 are configured in an array 22 of aligned columns 22c and rows 22r. In position (when assembled as will be discussed further below), the apertures 21 may cooperate with at least one adjacent card 10 to define portions of different and discrete flow channels or may cooperate to form a single or multiple flow channels.

FIG. 2B illustrates that each aperture 21 can have substantially the same width "W" and length "L" and that each aperture 21 can have the same geometric shape, e.g., a box-like shape, typically a square or rectangular shape. If the latter, the shape can have a width dimension (W) that is greater than a length dimension (L), although the reverse configuration or different shapes and dimensions may also be used. In particular embodiments, the gasket 20 can have a thickness 20t (FIG. 2A) that is between about 0.1 mm to about 12 mm, and may be typically between about 0.1 mm to about 10 mm. The width of the gasket aperture(s) 21 can also be called "GW."

In some embodiments, the material 15 discussed above with respect to the card 10, can instead or additionally be applied in or onto an inner surface of the gasket 20 (e.g., on a surface facing the card when assembled).

FIG. 3A illustrates that a gasket 20 can be attached to a corresponding card 10 so that apertures 11, 21 are aligned. The gasket and card 20, can define a gasket card pair or a biochip subassembly 30. The gasket card pair or subassembly 30 can be integral, e.g., non-detachable or releasably attached together. In some embodiments, the test sites 18s of the gasket and card pair 30 are analyzed without requiring disassembly of the two components 10, 20. As shown in FIGS. 3B and 3C, the test surface sites 18s are exposed or reside under the gasket apertures 21 proximate the card apertures 11. The card apertures 11 can be smaller than the overlying gasket apertures 21.

In some embodiments, at least some of the gasket apertures 21 have an area (e.g., defined by L and W) that is greater than the area (e.g., defined by L and W) of a card aperture 11. The area of some of the gasket apertures 21 can be greater than the area of at least some of the card apertures 11 by at least about 5%, typically by greater than 10%, such as for example, between about 15% to about 200%, but may greater than one or more of: about 20%, about 25%, about 30%, about 35%, 40%, 45%, 50%, 60%, 70%, 80%, 90%, 100%, according to particular applications.

In certain embodiments of the gasket/card pairs 30, a major portion, typically all or substantially all of the gasket apertures 21 of a gasket 20 can have substantially the same shape and/or size. Furthermore, in some embodiments, a major portion, typically all or substantially all of the card apertures 11 of the card 10, can have substantially the same shape and/or size. The area of the gasket apertures 21 is greater than the area of the card apertures 11, thereby exposing a substantially horizontal surface of each card 14 to a fluid sample flowing through a microfluidic flow channel created by alignment of the apertures of each gasket/card pair in the biochip 50, shown, for example, in FIGS. 4, 5A and 5B.

The shape of the apertures 11, 21 in the card 10 or gasket 21 can be any shape (e.g., box, rectangle, oval, circle, etc.). In an exemplary embodiment, the gasket aperture 21 has a box shape and the card aperture 11 has a rectangular shape with a width dimension (CW) being less than a width dimension of the gasket aperture (GW). As shown in FIG. 3C, attachment of the gasket 20 to a corresponding card 10 results in alignment of the (box shape) gasket apertures 21 over a corresponding one of the (rectangular shape) card apertures 11 such that a (horizontal) surface 14 of the card under the gasket 20 and a portion of or all of the rectangle shape card aperture 11 is exposed in the window or opening of the (box shape) gasket aperture 21 thereby defining an analytical site 18s on the card 10 and a portion of a (micro) fluidic flow channel 75 (FIG. 9).

FIGS. 4, 5A and 5B illustrate that the gasket/card pairs 30 can be assembled together into a stack to produce a three or four-dimensional biochip 50 having fluidic flow channels 75 (FIGS. 8, 9) passing therethrough. The gasket/card pairs 30 can be compressed together to define the multiple fluidic flow channels 75 through which multiple different fluid samples can be passed wherein such channels 75 may be configured to be discrete and isolated from one another to minimize or prevent contamination of different channels with the same fluid sample. In other embodiments, one set of apertures 11, 21 can be in fluid communication with another set to form a longer fluid flow channel (not shown).

FIG. 6 illustrates that each card 10 can define a different test (e.g., comprise a different material 15), so that a biochip 50 can carry out a number of different tests 60n e.g., tests n=1, to n, shown here as 10 tests (e.g., 10 cards). Also, each set of apertures 75s residing in fluid communication in an X-Y location (row and column) of the biochip 50 can define a different sample flow channel 75 allowing for a relatively large number of test samples 70n to pass through the biochip 50, where n=1, to the number or channels 75, shown here as 96 (8 columns and 12 rows, 8×12).

Advantageously, the biochip assemblies 30 selected to form the biochip 50 can be customized for a user and/or for the desired tests. As such, the biochip subassemblies 30 can be supplied individually or in related groups to a test site or preassembled to form a desired test kit or biochip 50.

In some embodiments, the biochips 50 can comprise a plurality of cards 10 and gaskets 20, x, wherein x is an integer from two to 100,000. For example, x can be three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 36, 47, 48, 49, 50, 75, 100, 150, 200, 250, 300, 350, 400, 450, 500, 1000, 10,000, 20,000, 30,000, 40,000, 50,000, 60,000, 70,000, 80,000, 90,000 or 100,000, including any number between the numbers recited herein but not specifically recited herein.

Furthermore, the biochips can comprise a plurality of card apertures 11, y, wherein y is an integer from one to about 100,000, typically between about two to about 1,536. In addition, the biochip can comprise a plurality of gasket apertures 21, z, wherein z is an integer from one to about 100,000, typically also between about two to about 1,536. For example, y and/or z can be three, four, five, six, seven, eight, nine, ten, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500 or 2000, including any number between the numbers recited herein but not specifically recited herein.

FIGS. 7A-7C illustrate a sequence of operations that can be used to form a biochip 50. In some embodiments, the cards 10 can be cleaned and coated with the bioactive material 15, such as with reagents, e.g., antibodies, or antigens, or other desired material. A corresponding gasket 20 can be attached to the card 10 to form the gasket/card pair 30. The pairs 30 are aligned and stacked to form the biochip 50. The cards 10 and gaskets 20 and/or gasket card pairs 30 can be held in a sterile environment or package to inhibit or assure no contamination during fabrication. In some embodiments, the gasket 20 is positioned over the corresponding card 10 such that a gasket aperture 21 resides over a corresponding card aperture 11 so that the card aperture 11 is positioned or resides proximate a side edge of the gasket aperture 21 and a substantially horizontal surface of the card 14 is exposed and is accessible for contact with a fluid sample or solution 70.

FIGS. 8 and 9 illustrate that, in some embodiments, the fluidic flow channels 75 have a repeating pattern of alternating substantially horizontal 75h and substantially vertical segments 75v extending along substantially the entire length of a respective channel 75. The flow channels 75 are defined by sets 75s of aligned card 11 and gasket apertures 21 from the different card and gasket pairs 30.

As shown by the top card in FIG. 9, at least one of the horizontal segments 75h associated with an upper surface 14 of a card 10 defines a horizontal test surface 18 or analytical site 18s that contacts or is accessible to a fluid test sample 70 flowing through the flow channel 75. This configuration can be repeated at each layer of the stacked biochip 50.

In some embodiments of the invention, the flow channel 75 is configured to extend upward or downward for a first distance corresponding to a thickness 10t of a first card 10, laterally for a second distance along a substantially horizontal surface of the first card, the second distance corresponding to a width of a first gasket aperture (GW), then extend upward or downward for a third distance corresponding to a thickness of a second card 10t, then laterally for a fourth distance along a substantially horizontal surface of the second card, the fourth distance corresponding to a width of a second gasket aperture (GW or second GW), wherein each channel is configured so that a fluid will travel substantially vertically for the first distance, substantially horizontally for the second distance, substantially vertically for the third distance and substantially horizontally for the fourth distance.

FIGS. 10A and 10B illustrate that the surface 18s of the card 10 will generate a signal that is an optically and/or electronically readable indicator of a positive or negative indication of the presence or absence of a condition or constituent in the sample. That is, for example, as the sample fluid 70 flows through the channel 75, antigens and/or antibodies in the sample will react with corresponding antigens and/or antibodies on the surface of the card 10 at the test site(s) 18s. The (flat) top surface 14 of the card 10 generates the signal at the test sites 18s that can be detected or read optically or electronically.

FIGS. 11 and 12 illustrate a partial cutaway view of the biochip 50. Referring to FIG. 12, the orientation of the apertures of the different cards 10 alternates on the sides of the fluid channels 75 as indicated by the circles on the left and right side of the channel 75. That is, as shown, the fluid channels 75 are defined by different layers of the cards 10 and gaskets 20 with one card aperture 11 residing on a left hand side 11l of the flow channel 75 and the next adjacent card aperture 11 residing on a right hand side 11r of the flow channel 75, aligned with the corresponding outer side edge of the gasket aperture 21.

To form the alternating configuration, the gasket and card pairs 30 can be assembled to align with the gasket apertures differently. That is, a first card 10 can be assembled to the corresponding gasket 20 so that the card apertures 11 reside on a right hand side 11r under and aligned with an outer edge of the right hand side of gasket aperture 21. The second card 10 can be assembled the corresponding gasket 20 so that the card apertures 11 reside on a left hand side 11l with an outer edge thereof under and aligned with a left side edge of the gasket apertures 21. Thus a biochip 50 can comprise a plurality of biochip subassemblies 30 in a stacked relationship and arranged so that adjacent first and second biochip subassemblies 30 are configured with the first biochip subassembly 30, having card apertures 11 proximate a left side of first gasket apertures 21 and the second biochip subassembly 302 having card apertures positioned proximate a right side of second gasket apertures, to form the (micro) fluidic flow channels as shown in FIGS. 11 and 12.

FIG. 13 illustrates an exemplary flow path 75 defined by the stacked cards 10. FIG. 13 also illustrates that each flow channel 75 of the biochip 50 is in communication with the fluid entry 140 (for fluid sample 70) on one side (shown as the lower side) and a fluid outlet port 150 on the other side (into a waste reservoir or other storage container).

In FIG. 6, the biochip 50 can have a surface comprising predetermined electronically and/or optically readable indicia 200. Such indicia 200 can be placed on or in the card during manufacture of the card 10 or biochip 50 and/or such indicia 200 can be placed on or in the card 10 after manufacture in the form of bar code, color code, symbols, watermark, icons, and/or a microchip with a secure "electronic handshake" or interface that communicates with an automated reader or analyzer. The location of the indicia 200 may be such that it is not readily visually apparent by the naked eye, and may be varied card-to-card 10 or biochip-to-biochip 50. The location of the indicia 200 may be electronically correlated via a batch or manufacturer code or the like. The indicia 200 can be in any form or in multiple forms for redundancy, e.g., a bar code, a sticker, plate, notch, etching, etc. These indicia 200 can be used, for example, to identify the card 10 and/or other characteristics of the biochip 50 containing the card (e.g., order or position in stack, identification of bioactive agent(s) or material(s) present on the card, status of testing of samples and/or analyzing of signal, etc.) and/or to verify the authenticity of the card or biochip containing the card 10, gasket 20 or the assembled biochip 50. These indicia 200 can be placed in any location (e.g., top, bottom, edge, under a gasket, on a gasket, on a test surface 18s) and can also be present at multiple locations on the same card 10, gasket 20 or biochip 50.

The indicia 200 can be visually, optically and/or electronically readable at the initiation of a test and/or before assembly of the cards 10 to verify the type of test thereon and/or the authenticity of the chip to help control counterfeit products and/or inaccurate testing. For example, an electronic detector or reader 400 (see, e.g., FIG. 18) can interrogate one or more cards 10 and identify whether the card or chip is an authorized or authentic card or chip. The reader can also be configured to alert a user when an unauthorized card or biochip is detected and may even be programmed to block an analysis of such a card or biochip or prominently disclaim the test results where such authenticity is questioned. This may allow a clinician or laboratory technician or other user to retest a sample or investigate the test results rather than rely on potentially false test analysis.

Figure 14:
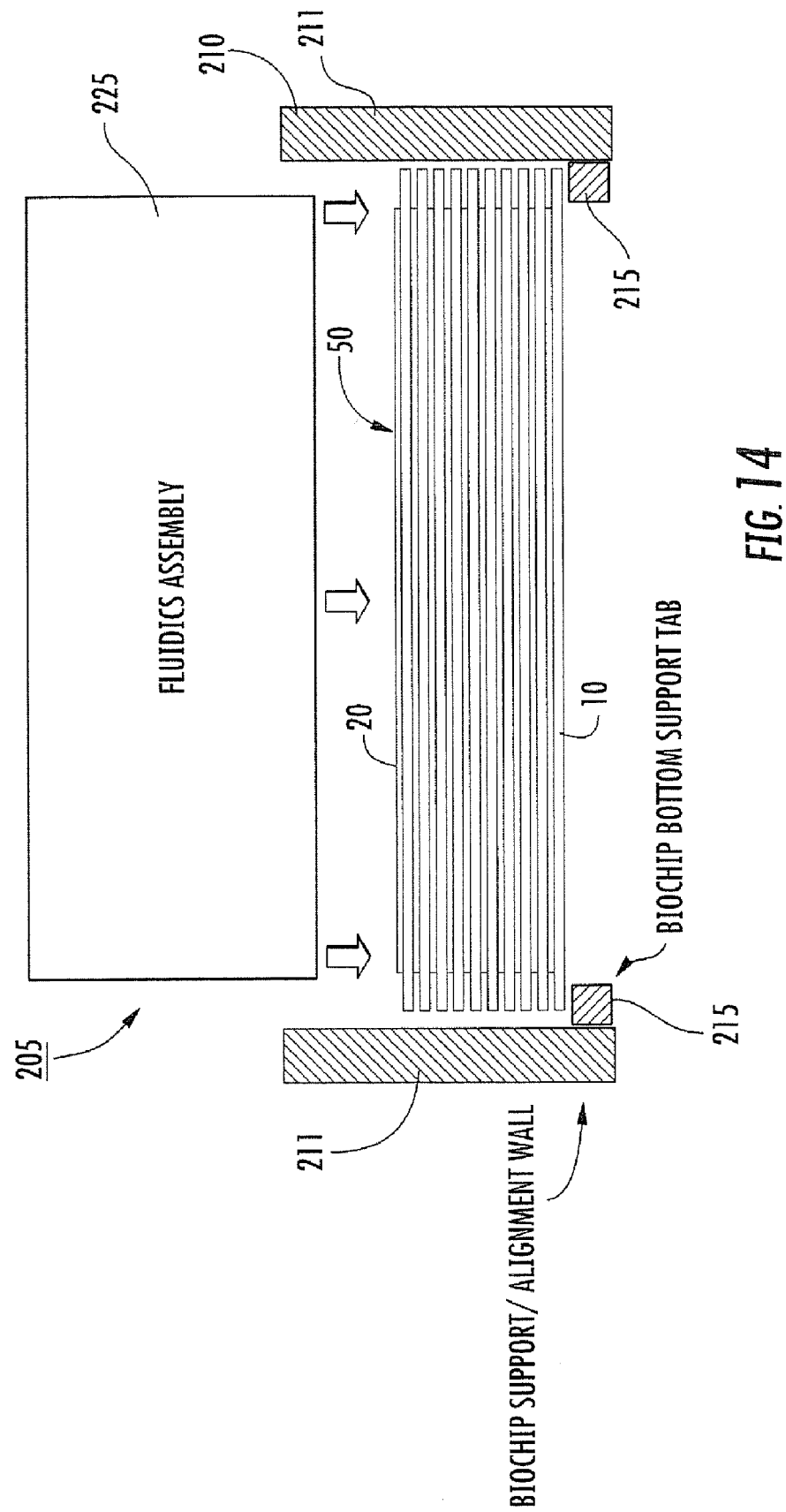
FIG. 14 is a schematic of an exemplary biochip in position in a biochip support and in communication with a fluid delivery system according to embodiments of the present invention.

FIG. 14 illustrates a biochip holder 205. As shown, the holder 205 includes a support housing 210 that is sized and configured to hold the biochip 50 securely therein. The housing 210 includes upstanding walls 211 on two, three or all four sides. A fluidics assembly 225 resides over the housing above the biochip 50. The fluidics assembly 225 can sealably engage the top gasket 20 and can cause the fluid sample(s) 70 to flow through the biochip 50 as is well known to those of skill in the art. In some embodiments, the housing 210 can include laterally extending tabs 215 that can retract to allow for disassembly of the card 10 or card/gasket pairs 30, one at a time. The height of the biochips 50 may vary in use depending on the number of cards in the biochip 50 which can vary test-to-test or user-to-user. The fluidics assembly 225 resides in fluid communication with one or more of the flow channels 75 at an upper surface of the biochip 50 and can be vertically adjustable to accommodate the variation in height of the biochip 50.

Figure 15A:
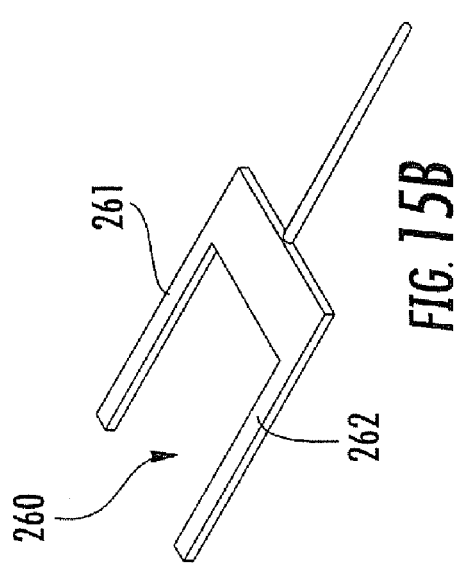
FIG. 15A is a top view of an example of a holding member according to embodiments of the present invention.
Figure 15B:
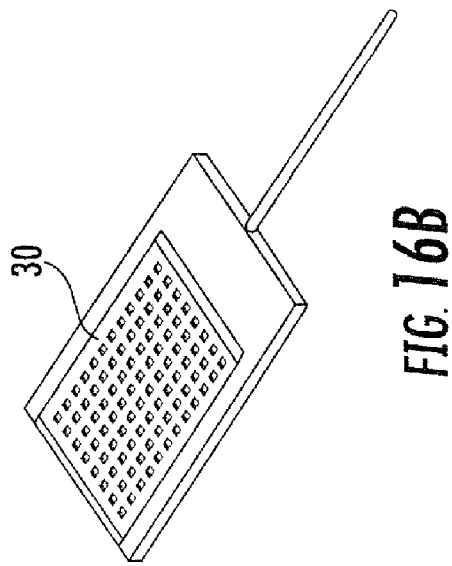
FIG. 15B is an isometric view of the exemplary holding member shown in FIG. 15A.
Figure 16A:
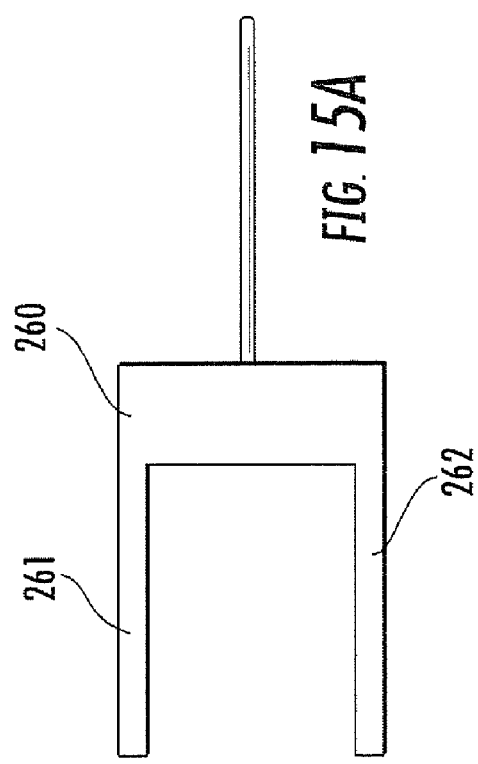
FIG. 16A is a top view of a holding member shown in FIGS. 15A and 15B holding a card (and gasket) according to embodiments of the present invention.
Figure 16B:
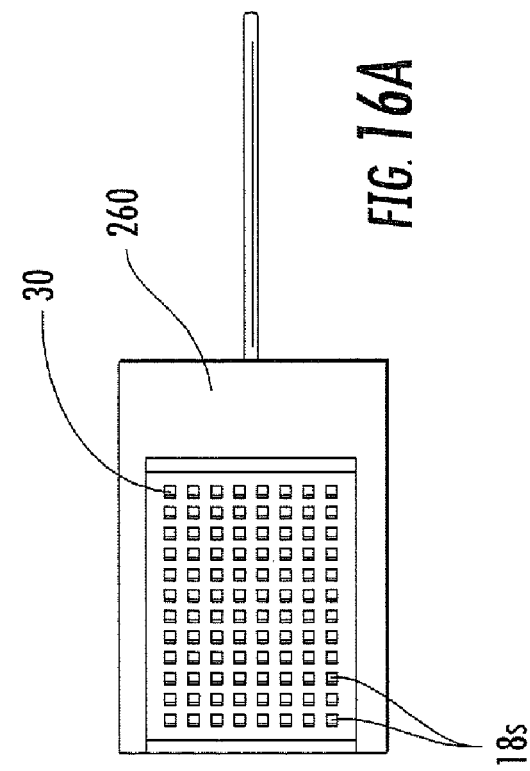
FIG. 16B is an isometric view of the holding member and card shown in FIG. 16A.

FIGS. 15A and 15B illustrate an example of a holding member 260 that is configured to hold a respective card 10 or card/gasket pair 30 and serially present a card 10 or card/gasket pair 30 to an electronic reader or detector 400 at a detection station 400s (FIG. 18) for interrogation, signal detection and/or analysis. The holding member 260 can include two spaced apart arms 261, 262 that hold opposing edges of the card 10 or card/gasket pair 30 without visually occluding the test analysis surface 18 for detection/analysis. The holding member 260 can be open in the middle under the card 10 as shown or may be closed or partially closed. FIGS. 16A and 16B illustrate a card in position on the holding member 260.

Figure 18:
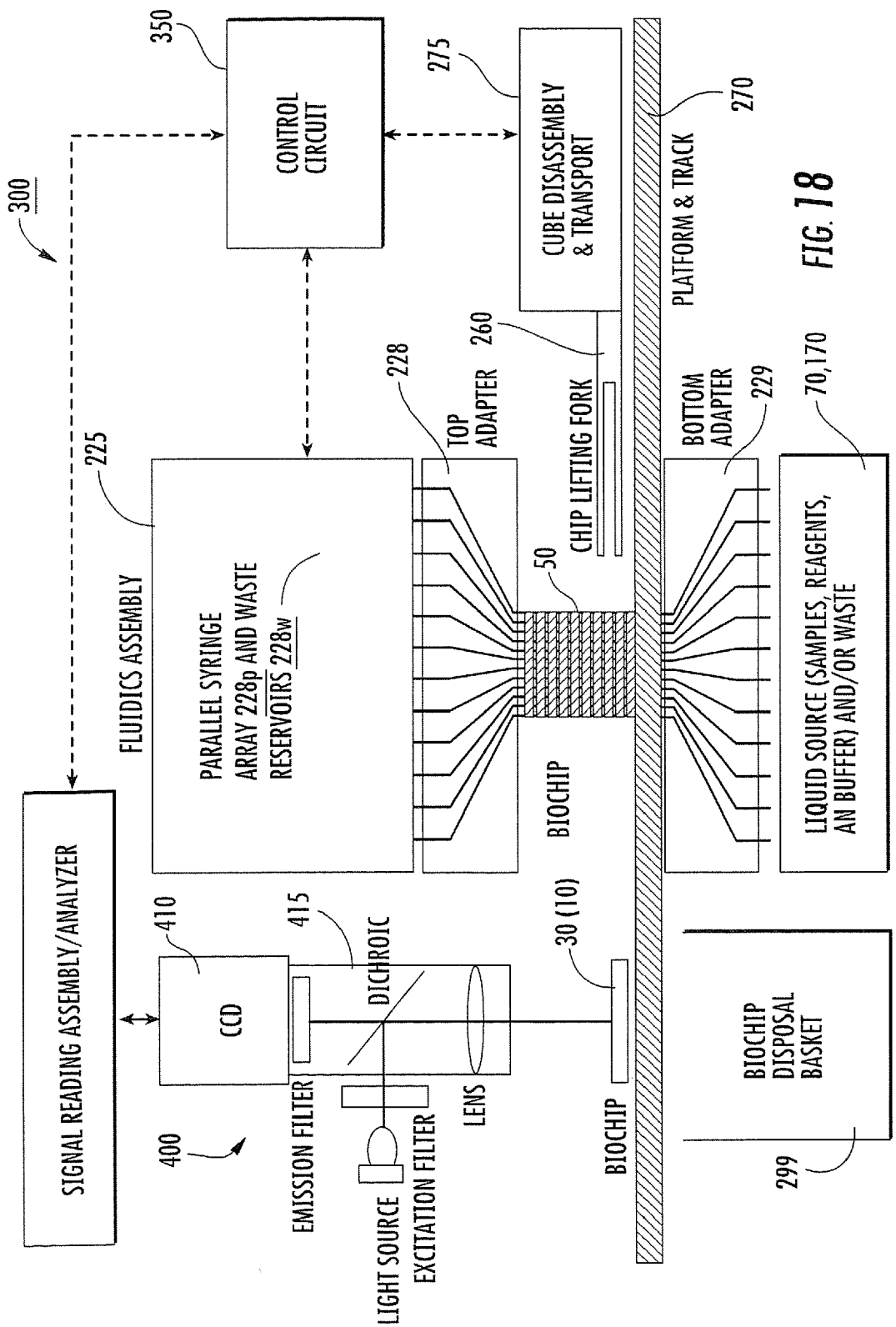
FIG. 18 is a schematic illustration showing an automated bioanalyzer according to embodiments of the present invention.

FIG. 17 illustrates an exemplary operation of the holding member 260 as it cooperates with the housing 205 to serially release and obtain a card or gasket pair 30. The holding member 260 can be in communication with a drive system 275 such as a belt or link drive, conveyor, or linear actuator that moves the device between stations. The holding member 260 can be oriented to be substantially horizontal and slide over a platform on a track under the housing 205 to obtain the card 10 or card/gasket pair and retrieve the card 10 or card/gasket pair 30 and present it to the detection station 400s (FIG. 18). The holding member 260 can have a home position 260h where it rests during inactive periods. The holding member 260 can present the card 10 or card/gasket pair 30 to the detector/reader in other orientations. The housing 210 can also release the cards or pair 10 from the top rather than the bottom or may be turned after use to dispense the cards 10 and/or card/gasket pairs 30 from a side (not shown).

Thus, FIG. 17 illustrates an empty holding member on the right, which, according to one embodiment of the invention, is automatically inserted into a biochip secured to a fluid delivery system as shown by the arrow cooperating with the retraction of the tabs 215 resulting in the release of a single card 10 and/or card gasket pair 30 of the biochip onto the holding member 260 for presentation to a signal reader 400. However, the automated analyzer 300, shown in FIG. 18, is not limited to the configuration shown as other housing disassembly and transport devices and configurations may be used.

In some embodiments, the gasket 20 can be removed or remain integrated with the respective card during reading. In addition, the biochip 50 may have a "dummy" card or "dummy" surface at one layer and/or optically or electronically readable indicia at one or each card layer to provide the authenticity verification marks and test identifiers discussed above.

FIG. 18 illustrates an automated or semi-automated analyzer 300. As shown, the analyzer 300 includes a fluidics assembly 225 with a top adaptor 228 in fluid communication with the channels of the biochip 50 and a lower adaptor 229 in fluid communication with the channels 75 of the biochip. The top adaptor 228 can communicate with a parallel syringe array 228s and one or more waste reservoirs 228w. The bottom adaptor 229 can have different flow channels that communicate with the entry ports of the biochip flow channels 75. The bottom adaptor 229 can be in fluid communication with the fluid source(s), e.g., samples, reagents, buffers, and/or waste. The analyzer 300 includes a signal reader or detector 400 at a reading or detection station 400s. The signal reader or detector 400 can include a CCD (charge coupled device) instrument and optic circuits such as filters and lenses that optically communicate with the test surface 18s of the card 10. Other signal readers or detectors may be used, such as, but not limited, to optic image recognition systems, intensity, luminescence, radioactivity, magnetism, mass, fluorescence, or color detectors and the like (or combinations of different types of signal detectors and readers). The system 300 can include a biochip waste disposal 299 that collects used cards or card/gasket pairs 30 so that a user can avoid contact therewith. The biochip holder 260 can obtain and present the cards 10 to the reader/detector 400. The signal reader 400 can include an analyzer that analyzes the signal of the different test sites or the analyzer may be remote. The analyzer can include a programmatic library of signals (not shown) that correlate detected signals to a positive or negative condition for each test. The biochip cards 10 and/or card/gasket pair 30 and reader 400 can cooperate to electronically correlate a sample and a test to the location of the test site 18s on the card 10 and the test type based on the material 15 and/or sample 70.

The signal reader 400 can selectively engage all or select ones of the analytical sites 18s of a card 10 of the biochip 50 and detect and/or obtain a signal from the analytical site 18s. The signal reader can be in communication with a control circuit 350 configured to direct automated operation of the analyzer 300 to serially obtain one card and present the obtained card to the signal reader and analyze the obtained signal. In embodiments in which one or more than one card 10 of the biochip 50 comprises predetermined optically and/or electronically readable indicia as described herein, the control circuit 350 of the analyzer 300 can comprise a controller that is configured to direct the signal reader to obtain signal from the region(s) of the card comprising such indicia.

The card/gasket pairs 30 can be releasably attached in the stacked biochip so that one or more cards can be removed from the biochip separately, sequentially, or in any order or combination. Furthermore, the first card/gasket pair can be configured with a first card aperture 11 located proximate the left side of a first gasket aperture 21 and a second card/gasket pair can be configured with a second card aperture 11 located proximate the right side of a second gasket aperture 21, etc., for subsequent alternating card/gasket pairs to define (micro) fluidic flow channels 75 with alternating substantially horizontal and substantially vertical surfaces. To obtain the desired layer orientation during assembly/stacking, the card and gasket pairs 30 can be assembled the same way irrespective of its subsequent position in the assembly/stack (e.g., without regard to orientation of the card aperture relative to the gasket aperture). During assembly, one card and gasket pair 30 can be rotated 180 degrees relative to the next adjacent pair 30 to alternately position the card aperture at either the left hand side or the right side of the corresponding gasket apertures 21. If a laboratory or end user will be assembling the devices, assembly orientation indicia can be marked on the card/gasket pairs to facilitate proper orientation.

Figure 19:
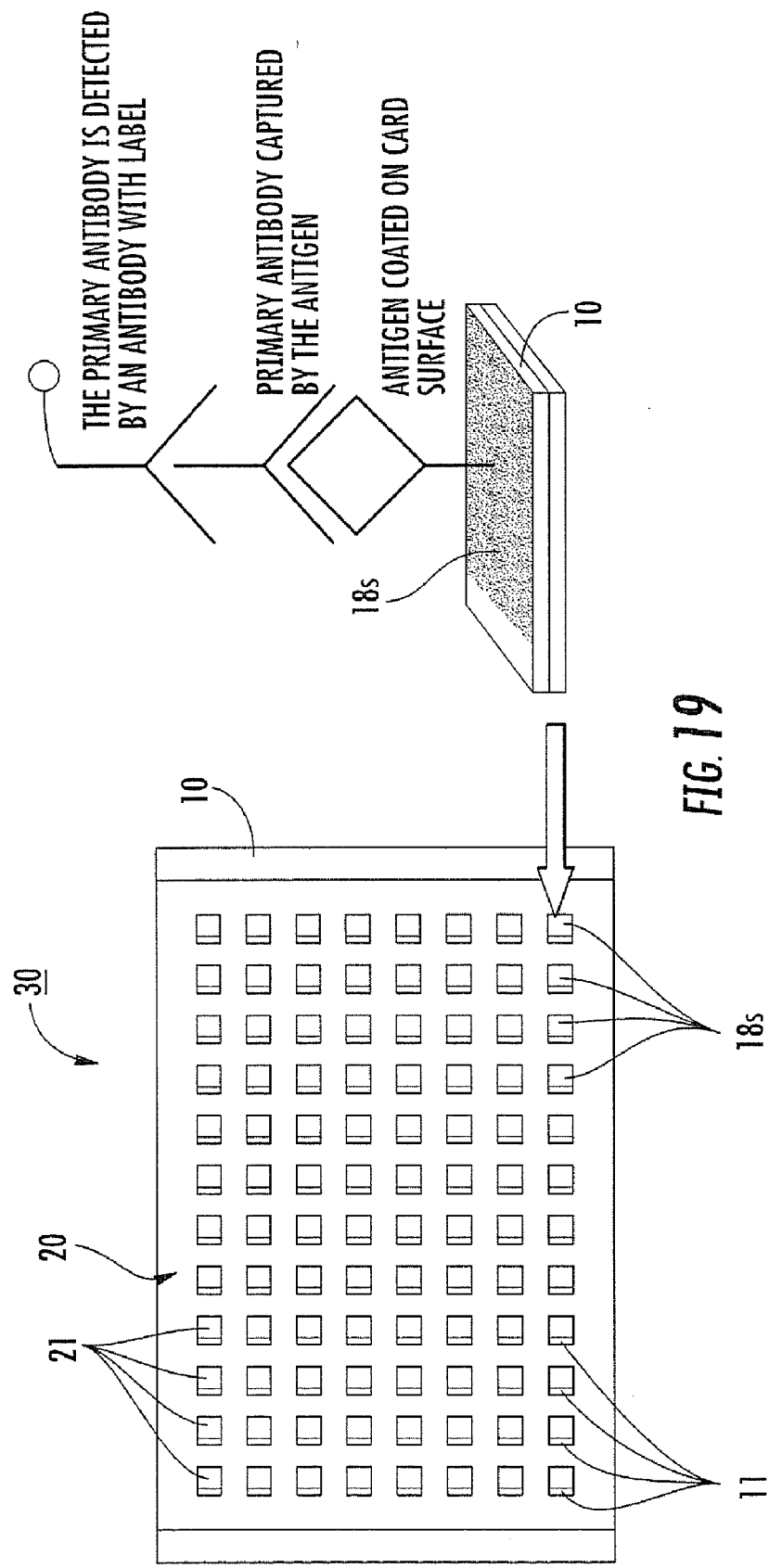
FIG. 19 is a schematic illustration of a biochip configured with immunoassays according to embodiments of the invention.

FIG. 19 illustrates one exemplary embodiment wherein a target antibody can be detected in a sample following flow of the sample through a microfluidic flow channel 75 of a biochip 50, formation of an antigen/antibody complex as a result of the capture of the antibody by an antigen immobilized to a test surface 18s of a card 10 and subsequent capture of a detectably labeled antibody by the antigen/antibody complex.

Figure 20:
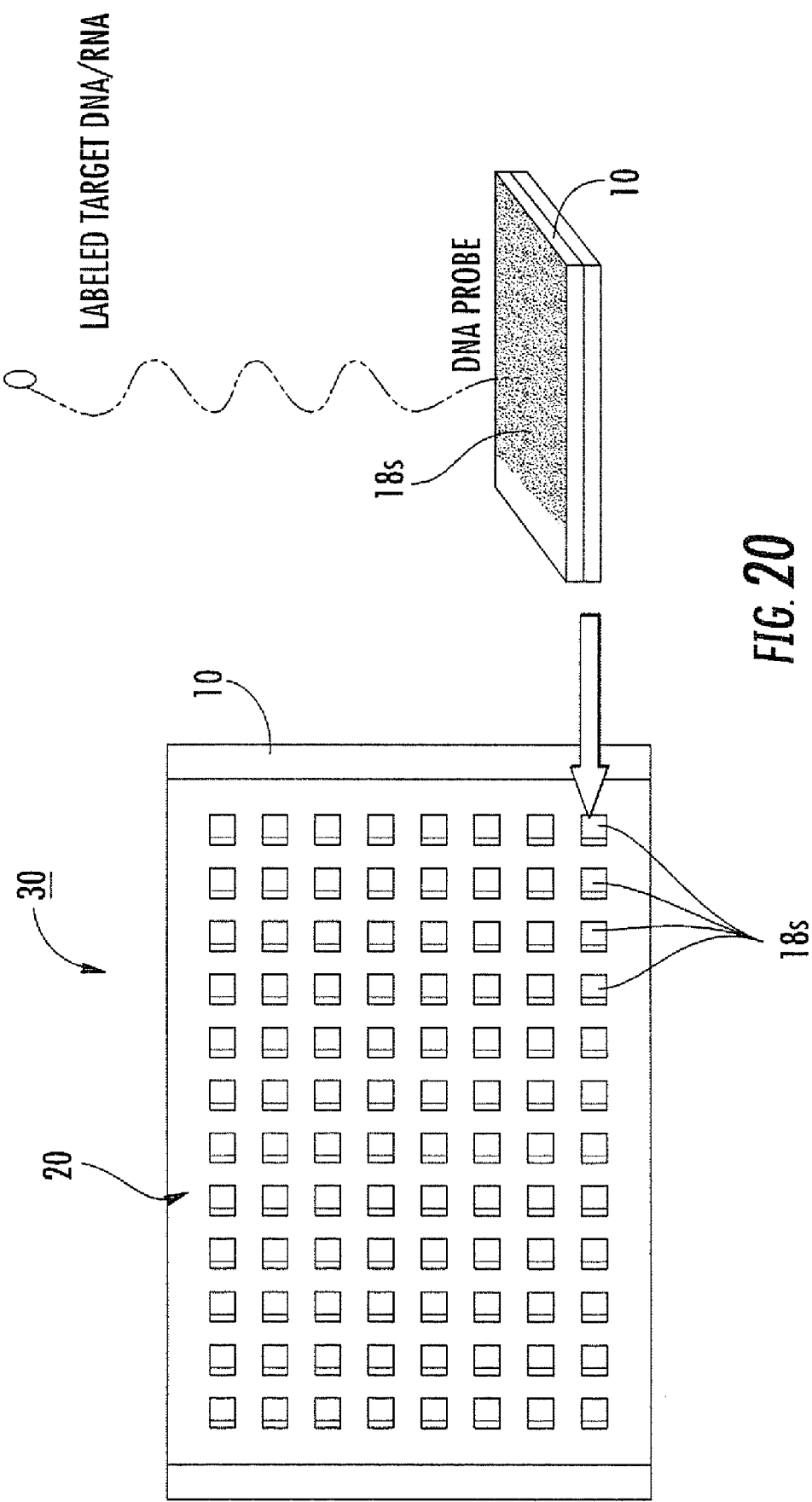
FIG. 20 is a schematic illustration of a biochip configured to provide nucleic acid hybridization assays according to embodiments of the present invention.

FIG. 20 illustrates another exemplary embodiment wherein a target nucleic acid can be detected in a sample following flow of the sample through a microfluidic flow channel 75, formation of a nucleic acid hybridization complex as a result of hybridization between the target nucleic acid and a probe nucleic acid immobilized to a surface 18s of a card 10 of the biochip 50 and subsequent detection of the hybridization complex.

Further embodiments of this invention include an automated method of analyzing multiple samples exposed to multiple analytical sites in a biochip, comprising: a) introducing a multiplicity of fluid samples into a fluid delivery system of an automated bioanalyzer; b) flowing the multiplicity of fluid samples through a biochip having a plurality of releasably attached card/gasket pairs, each of the card/gasket pairs having an aligned array of apertures extending therethrough, wherein sets of the apertures define microfluidic flow channels, wherein at least one card of the biochip comprises at least one bioactive agent or material on at least one of an upper and lower surface that contacts a sample flowing thereover, with each card comprising said agent and/or material defining at least one analytical site in the channels proximate the card apertures; c) serially obtaining and presenting a card of the biochip to a signal reader configured to selectively engage at least one analytical site of the card and obtain a signal from the analytical site; d) selectively engaging the at least one analytical site of the respective cards and obtaining a signal from the analytical site; and e) analyzing the obtained signal.

In a stacked biochip comprising multiple cards, one or more different cards can comprise a different bioactive agent or material so that multiple different analyses can be conducted in the same biochip. Such a biochip can also comprise multiple microfluidic flow channels so that multiple different samples can be tested for multiple different analytes in the same biochip 50.

Nonlimiting examples of a bioactive agent or material of this invention include an antibody, an antigen, a nucleic acid, a peptide nucleic acid, a ligand, a receptor, avidin, streptavidin, biotin, Protein A, Protein G, Protein L, a substrate for an enzyme, an anti-antibody, a toxin, a peptide, an oligonucleotide and any combination thereof.

The bioactive agent or material can be attached directly to the card and/or the bioactive agent or material can be attached to the card indirectly (i.e., via a linker such as PEG (polyethylene glycol), EDC (N-3-Dimethylaminopropyl-N'-ethylcarbodiimide hydrochloride), lutaraldehyde, etc.). The bioactive agent can also be attached to the card through a mediate layer of biotin, avidin, polylysine, BSA (bovine serum albumin), etc. as is known in the art. The bioactive agent or material of this invention can also be provided to an analytical site in a fluid solution, e.g., in order to detect a reaction at the analytical site.

In some embodiments, the bioactive material can be an antibody or antibody fragment and a signal is detected if an antigen/antibody complex is formed. In such embodiments, as an example, a first antibody or antibody fragment can be attached directly or indirectly to a card of the biochip via any variety of attachment protocols standard in the art. Then a fluid test sample is passed through a microfluidic flow channel of the biochip such that the sample contacts an analytical site on the card that comprises the immobilized first antibody or antibody fragment. If there is an antigen in the test sample that is specific for the immobilized first antibody or antibody fragment, the antigen will be bound (i.e., "captured") by the immobilized first antibody or antibody fragment, resulting in the formation of an antigen/antibody complex immobilized on the card. A fluid comprising a second antibody or antibody fragment that is detectably labeled is then passed through the microfluidic flow channel. The detectably labeled second antibody or antibody fragment is also specific for the antigen bound by the first immobilized antibody and will therefore bind to the captured antigen, thereby immobilizing the detectably labeled second antibody or antibody fragment at the analytical site. Upon subsequent analysis of the card, the immobilized detectably labeled second antibody is detected at the analytical site according to the methods described herein and as are well known in the art for such detection. The result of the analytical testing is that the test sample comprises (e.g., is positive for) the target antigen.

In some embodiments, the bioactive material can be an antigen and a signal is detected if an antigen/antibody complex is formed. In such embodiments, as an example, an antigen (e.g., a peptide, polypeptide, amino acid sequence defining an epitope, etc.) is attached directly or indirectly to a card of the biochip via any variety of attachment protocols standard in the art. Then a fluid test sample is passed through a microfluidic flow channel of the biochip such that the sample contacts an analytical site on the card that comprises the immobilized antigen. If there is an antibody in the test sample that is specific for the immobilized antigen, the antibody in the sample will be bound (i.e., "captured") by the immobilized antigen, resulting in formation of an antigen/antibody complex immobilized on the card. A fluid comprising a detectably labeled anti-antibody or antibody fragment specific for an antibody of the species from which the test sample was obtained is then passed through the microfluidic flow channel. The detectably labeled antibody or antibody fragment will bind the immobilized antibody captured by the antigen, thereby immobilizing the detectably labeled antibody or antibody fragment at the analytical site. Upon subsequent analysis of the card, the immobilized detectably labeled antibody is detected at the analytical site according to the methods described herein and as are well known in the art for such detection. The result of the analytical testing is that the test sample comprises (e.g., is positive for) the target antibody.

In other embodiments, the bioactive material can be a nucleic acid or peptide nucleic acid and a signal is detected if a nucleic acid hybridization complex is formed. In such embodiments, as an example, a nucleic acid (e.g., an oligonucleotide) or peptide nucleic acid (PNA) is attached directly or indirectly to a card of the biochip via any variety of attachment protocols standard in the art. Then a fluid test sample is passed through a microfluidic flow channel of the biochip such that the sample contacts an analytical site on the card that comprises the immobilized nucleic acid or PNA. If there is a nucleic acid in the test sample that is complementary [either fully complementary or of sufficient partial complementarity to form a hybridization complex under the conditions of the assay (e.g., high stringency, medium stringency or low stringency as such terms are known in the art)], the nucleic acid in the sample will hybridize to (i.e., "be captured by") the immobilized nucleic acid or PNA, resulting in formation of a hybridization complex immobilized on the card. Upon subsequent analysis of the card, the immobilized hybridization complex is detected at the analytical site according to the methods described herein and as are well known in the art for such detection. The result of the analytical testing is that the test sample comprises (e.g., is positive for) the target nucleic acid. In some embodiments, the immobilized hybridization complex can be detected because the nucleic acid in the test sample has been modified to comprise a detectable signal (e.g., fluorescence, chemiluminescence, radioactivity, electrochemical detection, enzymatic detection, magnetic detection, mass spectroscopy etc.).

The examples set forth above describing various assays that can be carried out in the biochip of this invention are not intended to be limiting in any way. If a target analyte can be captured by a corresponding bioactive agent that can be attached on the card, and the analyte can be detected by one of the detection methods listed above or other methods, then the assay can be performed on the biochip according to embodiments of this invention. The biochips can be employed to carry out any type of direct immunoassay, indirect immunoassay, competitive binding assay, neutralization assay, diagnostic assay, and/or biochemical assay. For example, a prenatal and/or neonatal TORCH assay, antigens and/or antibodies specific to toxoplasmosis, rubella, cytomegalovirus and herpes simplex virus can be attached on the cards for capturing both IgG and IgM antibodies and/or viral antigens corresponding to the pathogens in human serum. As another example, antibodies and/or antigens specific to human Hepatitis B and C can be attached on the cards for detecting antibodies specific to surface and core antigens of the virus and/or the antigens in human serum samples. Another example, a substrate is immobilized on the card and a fluid sample is passed over the immobilized substrate to detect an enzyme that specifically acts on the immobilized substrate. A product of such enzyme activity can be detected, resulting in the identification of a test sample positive for the target enzyme.

Nonlimiting examples of pathogens, agents of interest and/or contaminants that can be detected, identified and/or quantitated according to methods and devices of embodiments of the inventions include a majority of pathogens causing infectious diseases in human and animal, food borne pathogens, and pathogens which can be used as bioterrorism agents. The biochips can also be used to detect antibodies and proteins which can be used to diagnose a majority of infectious diseases and other diseases and conditions (e.g. thyroid function, pregnancy, cancers, cardiac disorders, autoimmune diseases, allergy, therapeutic drug monitoring, drug abuse tests, etc.). It would be well understood to one of ordinary skill in the art that the methods and biochips according to embodiments of this invention can also be employed to detect, identify and/or quantitate specific nucleic acids in a sample (e.g., mutations such as insertions, deletions, substitutions, rearrangements, etc., as well as allelic variants (e.g., single nucleotide polymorphisms). Nucleic acid based assays of embodiments of this invention can also be employed as diagnostics (e.g., to detect nucleic acid of a pathogen in a sample). In some embodiments, mutations of cytochrome P450 genes and blood clotting factor genes can be detected and/or identified. The biochips of embodiments of this invention can also be used to determine the level of a RNA transcript by hybridizing a labeled complex mixture of RNA samples onto cards coated with complementary strands of oligonucleotides or cDNAc.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

What is claimed is:
1. A biochip, comprising:
a plurality of cards, each card having a plurality of card apertures extending therethrough, each respective card aperture having one or more cross sectional areas; and
a plurality of elastically compressible gaskets, at least one gasket residing intermediate two neighboring cards, each gasket having a plurality of gasket apertures extending therethrough, at least some of the gasket apertures having an area that is greater than that of at least one adjacent card aperture, wherein different sets of the gasket apertures and card apertures define a plurality of fluidic flow channels.

2. The biochip of claim 1, wherein the cards are rigid, wherein the cards and gaskets are releasably attached and held together in a stack to define microfluidic flow channels, and wherein at least some of the channels have a repeating pattern of alternating substantially horizontal and substantially vertical segments along substantially an entire length thereof, with at least one of the substantially horizontal segments associated with an upper or lower surface of a respective card defining a test surface that contacts a flowing test sample.

3. The biochip of claim 1, wherein one gasket is affixed to one card to define an integral gasket/card pair, with the gasket apertures aligned with corresponding card apertures, wherein a plurality of the gasket/card pairs are releasably engageable and held together to define the plurality of fluidic flow channels.

4. The biochip of claim 1, wherein the gaskets are configured with an array of gasket apertures with substantially all or all of the gasket apertures having the same shape and size, and wherein the cards are configured with an array of card apertures with substantially all or all of the card apertures having the same shape and size.

5. The biochip of claim 1, wherein the gasket apertures have a box shape, and wherein the card apertures are substantially rectangular with a length dimension thereof being greater than a width dimension thereof.

6. The biochip of claim 1, wherein at least some of the cards comprise at least one bioactive material on at least one of an upper and lower surface of the card that contacts a fluid sample flowing thereover.

7. The biochip of claim 1, wherein different cards have different bioactive materials to conduct multiple analyses.

8. The biochip of claim 1, wherein the biochip defines a plurality of different analytical sites, at least one on each card, and wherein the plurality of fluidic flow channels are in fluid isolation and configured to analyze a plurality of different samples.

9. The biochip of claim 8, wherein the biochip is configured to concurrently flowably receive the plurality of different samples, one through each fluidic flow channel and expose the respective samples to a plurality of different analytical sites, with at least one analytical site on each card in an area of the card on an upper or lower surface under or over and exposed by an aligned gasket aperture.

10. A biochip comprising a plurality of releasably engageable stacked cards with at least one gasket between neighboring cards with layers of gasket and cards defining microfluidic flow channels, wherein the channels extend upward or downward for a first distance corresponding to a thickness of a first card, laterally for a second distance along a substantially horizontal surface of the first card, the second distance corresponding to a width of a first gasket aperture, then extending upward or downward for a third distance corresponding to a thickness of a second card, then laterally for a fourth distance along a substantially horizontal surface of the second card, the fourth distance corresponding to a width of a second gasket aperture, wherein the gaskets are thermoplastic elastomer gaskets, wherein the gasket apertures have a box shape, and wherein the card apertures have a rectangular shape, with a width dimension of the card apertures being a minor portion of a width dimension of the gasket apertures, and with a length dimension of the card apertures being substantially the same as a length dimension of the gasket apertures.

11. The biochip of claim 10, wherein the stacked cards and gaskets define a regular repeating pattern of closely spaced microfluidic flow channels, wherein each channel is configured so that a fluid can travel substantially vertically for the first distance, substantially horizontally for the second distance, substantially vertically for the third distance, and substantially horizontally for the fourth distance.

12. A biochip, comprising:
a plurality of stackable card/gasket members, each member having an opposing upper and lower surface and a plurality of apertures extending therethrough, the stackable members being aligned so that the apertures define fluidic flow channels, wherein the channels have a series of repeating and alternating substantially horizontal and substantially vertical surfaces defined by adjacent card member and gasket member layers, with at least some of the substantially horizontal surfaces defining at least one analytical site having at least one bioactive material, wherein the card members are rigid members and the gasket members are elastically compressible members.

13. The biochip of claim 1 or 12, wherein a surface of one or more than one card comprises predetermined optically readable indicia.

14. The biochip of claim 1 or 12, comprising a plurality of cards and gaskets, x, wherein x is an integer from one to 100,000.

15. The biochip of claim 1 or 12, comprising a plurality of card apertures, y, wherein y is an integer from one to 1536.

16. The biochip of claim 1 or 12, comprising a plurality of gasket apertures, z, wherein z is an integer from one to 1536.

17. The biochip of claim 1 or 12, wherein each card of the plurality of cards has the same number of card apertures.

18. The biochip of claim 1 or 12, wherein the gaskets are thermoplastic elastomer gaskets, and wherein each gasket of the plurality of gaskets has the same number of gasket apertures.

19. The biochip of claim 1 or 12, wherein the number of card apertures of each card is equal to the number of gasket apertures of each gasket.

\* \* \* \* \*